US00PP27114P2

(12) United States Plant Patent
Eveleens

(10) Patent No.: US PP27,114 P2
(45) Date of Patent: Aug. 30, 2016

(54) CARNATION PLANT NAMED 'HILSOIMRE'

(50) Latin Name: *Dianthus caryophyllus*
Varietal Denomination: Hilsoimre

(71) Applicant: Peter Eveleens, Aalsmeer (NL)

(72) Inventor: Peter Eveleens, Aalsmeer (NL)

(73) Assignee: Hilverda Kooij B.V., De Kwakel (NL)

( * ) Notice: Subject to any disclaimer, the term of this patent is extended or adjusted under 35 U.S.C. 154(b) by 190 days.

(21) Appl. No.: 14/121,202

(22) Filed: Aug. 11, 2014

(51) Int. Cl.
*A01H 5/02* (2006.01)

(52) U.S. Cl.
USPC ..... Plt./273

(58) Field of Classification Search
USPC ..... Plt./273
See application file for complete search history.

*Primary Examiner* — Keith Robinson
(74) *Attorney, Agent, or Firm* — C. A. Whealy

(57) ABSTRACT

A new and distinct cultivar of Carnation plant named 'Hilsoimre', characterized by its upright plant habit; freely flowering habit; flat red purple-colored flowers with a single whorl of petals; flowers face mostly upright; and good post-production longevity.

1 Drawing Sheet

Botanical designation: *Dianthus caryophyllus.*
Cultivar denomination: 'HILSOIMRE'.

BACKGROUND OF THE INVENTION

The present invention relates to a new and distinct cultivar of Carnation plant, botanically known as *Dianthus caryophyllus*, grown commercially as a cut flower plant and hereinafter referred to by the name 'Hilsoimre'.

The new Carnation plant is a product of a planned breeding program conducted by the Inventor in De Kwakel, The Netherlands. The objective of the breeding program is to create new cut flower Carnation plants with numerous flat flowers with a single whorl of petals.

The new Carnation plant originated from a cross-pollination made by the Inventor in De Kwakel, The Netherlands in June, 2009 of a proprietary selection of *Dianthus caryophyllus* identified as code number WS 03-544, not patented, as the female, or seed, parent with a proprietary selection of *Dianthus caryophyllus* identified as code number WS 06-549, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2010.

Asexual reproduction of the new Carnation plant by terminal cuttings propagated in a controlled greenhouse environment in De Kwakel, The Netherlands since October, 2010 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilsoimre'. These characteristics in combination distinguish 'Hilsoimre' as a new and distinct Carnation plant:

1. Upright plant habit.
2. Freely flowering habit.
3. Flat red purple-colored flowers with a single whorl of petals; flowers face mostly upright.
4. Good postproduction longevity.

Plants of the new Carnation differ from plants of the female parent selection in the following characteristics:

1. Plants of the new Carnation are not as freely flowering as plants of the female parent selection.
2. Flowers of plants of the new Carnation face more upright than flowers of plants of the female parent selection.
3. Flower petals of plants of the new Carnation are red purple in color whereas flower petals of plants of the female parent selection are dark red in color.

Plants of the new Carnation differ from plants of the male parent selection in the following characteristics:

1. Plants of the new Carnation are not as freely flowering as plants of the male parent selection.
2. Flower petals of plants of the new Carnation are red purple in color whereas flower petals of plants of the male parent selection are light orange in color.

Plants of the new Carnation can be compared to plants of *Dianthus caryophyllus* 'Hilsogil', not patented. In side-by-side comparisons conducted in De Kwakel, The Netherlands, plants of the new Carnation differed from plants of 'Hilsogil' in the following characteristics:

1. Flowers of plants of the new Carnation faced more upright than flowers of plants of 'Hilsogil'.
2. Flower petals of plants of the new Carnation were red purple in color whereas flower petals of plants of 'Hilsogil' were light red in color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering stem of 'Hilsoimre'.

DETAILED BOTANICAL DESCRIPTION

Plants used in the aforementioned photograph and following observations and measurements were grown during the spring and early summer in ground beds in a glass-covered greenhouse in De Kwakel, The Netherlands and under cultural practices typical of commercial cut flower Carnation production. During the production of the plants, day temperatures ranged from 10° C. to 25° C. and night temperatures ranged from 8° C. to 12° C. Plants were pinched one time five weeks after planting. Plants used for the photograph and description were nine months old. In the following description, color references are made to The Royal Horticultural Society Colour Chart, 2007 Edition, except where general terms of ordinary dictionary significance are used.

Botanical classification: *Dianthus caryophyllus* 'Hilsoimre'.

Parentage:

*Female, or seed, parent*.—Proprietary selection of *Dianthus caryophyllus* identified as code number WS 03-544, not patented.

*Male, or pollen, parent*.—Proprietary selection of *Dianthus caryophyllus* identified as code number WS 06-549, not patented.

Propagation:

*Type*.—By terminal cuttings.

*Time to initiate roots, summer*.—About six days at temperatures about 20° C. to 25° C.

*Time to initiate roots, winter*.—About eight days at temperatures about 18° C.

*Time to produce a rooted young plant, summer*.—About three weeks at temperatures about 20° C. to 25° C.

*Time to produce a rooted young plant, winter*.—About five weeks at temperatures about 18° C.

*Root description*.—Medium in thickness, fibrous.

*Rooting habit*.—Moderate branching; medium density.

Plant description:

*Plant and growth habit*.—Herbaceous perennial, typically grown as a cut flower; upright plant habit; moderate to high vigor.

*Branching habit*.—About three main stems; each main stem with about five lateral branches.

*Plant height*.—About 94 cm.

*Plant diameter or spread*.—About 33.9 cm.

*Lateral branches*.—Length, main stems: About 67.8 cm. Length, lateral branches: About 27 cm. Diameter: About 3 mm. Internode length: About 7.6 cm. Strength: Strong. Texture: Smooth, glabrous; waxy. Color: Close to N137B; waxy cuticle, close to 189B.

Leaf description:

*Arrangement*.—Opposite, simple; sessile.

*Length*.—About 12.2 cm.

*Width*.—About 9 mm.

*Shape*.—Narrowly lanceolate.

*Apex*.—Narrowly acute.

*Base*.—Attenuate; decurrent.

*Margin*.—Entire.

*Texture, upper and lower surfaces*.—Smooth, glabrous; waxy.

*Venation pattern*.—Parallel.

*Color*.—Developing leaves, upper surface: Close to 143A; towards the base, close to 144C; waxy cuticle, close to 189A. Developing leaves, lower surface: Close to 137C; towards the base, close to 144C; waxy cuticle, close to 189A. Fully expanded leaves, upper and lower surfaces: Close to N137B; waxy cuticle, close to 189A to 189B; venation, same as lamina.

Flower description:

*Flower form and flowering habit*.—Rotate single flat flowers arranged in terminal panicles; freely flowering habit with typically about 21 flowers developing per inflorescence; flowers face mostly upright, that is, roughly horizontal.

*Fragrance*.—Moderate to strongly fragrant; clove-like, sweet.

*Natural flowering season*.—Flowering is continuous from the spring through the summer until late summer in The Netherlands; plants begin flowering about 32 weeks after planting.

*Postproduction longevity*.—Good postproduction longevity; inflorescences maintain good substance for about two to three weeks as a cut flower; flowers not persistent.

*Inflorescence height*.—About 26.8 cm.

*Inflorescence diameter*.—About 14.3 cm.

*Flower diameter*.—About 4.6 cm.

*Flower depth*.—About 3.9 cm.

*Flower buds*.—Length: About 2.1 cm. Diameter: About 9 mm. Shape: Oblong. Color: Close to 138A to 138B; base, close to 144A to 144B.

*Petals*.—Quantity and arrangement: About six petals arranged in a single whorl. Length: About 4.6 cm. Width: About 2.6 cm. Shape: Spatulate. Apex: Praemorse, slightly crinkled. Base: Acute. Margin: Entire. Texture, upper and lower surfaces: Smooth, glabrous; velvety. Color: When opening, upper surface: Close to N57B; towards the base, close to 149D. When opening, lower surface: Close to 58B and 58C; towards the base, close to 149D. Fully opened, upper surface: Close to N57A to N57B; towards the base, close to 149D; with development, main color becomes closer to N66B and 67B. Fully opened, lower surface: Close to N57D and 61D; towards the base, close to 149D.

*Sepals*.—Quantity and arrangement: Six in a single whorl; proximal 75% portions of the sepals are fused into a campanulate- shaped calyx. Length: About 2.8 cm. Width: About 7 mm. Shape: Oblong. Apex: Acute. Margin: Entire. Texture, upper and lower surfaces: Smooth, glabrous. Color: When opening, upper surface: Close to 191C to 191D; towards the apex, close to 138C. When opening, lower surface: Close to 138A and 138B; towards the base, close to 144A to 144B. Fully opened, upper surface: Close to 191C to 191D; towards the apex, close to 138C. Fully opened, lower surface: Close to 137B; towards the base, close to 144B.

*Peduncles*.—Length: About 24.5 cm. Diameter: About 2.5 mm. Strength: Strong. Aspect: Erect to about 25° from vertical. Texture: Smooth, glabrous; waxy. Color: Close to N137C; waxy cuticle, close to 189B.

*Pedicels*.—Length: About 1.3 cm. Diameter: About 2 mm. Strength: Strong. Aspect: Erect to about 30° from vertical. Texture: Smooth, glabrous; waxy. Color: Close to 143B to 143C; waxy cuticle, close to 189B.

*Reproductive organs*.—Stamens: Quantity: About twelve per flower. Filament length: About 3.1 cm. Filament color: Close to 157D. Anther length: About 3.5 mm. Anther shape: Elliptic. Anther color: Close to 156C. Pollen: Abundant. Pollen color: Close to 156B to 156C. Pistils: Quantity: About three per flower. Pistil length: About 1.3 cm. Stigma shape: Pointed, curved. Stigma color: Close to N155A. Style length: About 1.2 cm. Style color: Close to NN155A. Ovary color: Close to 144B to 144C. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be hardy to USDA Hardiness Zone 9.

It is claimed:

1. A new and distinct Carnation plant named 'Hilsoimre' as illustrated and described.

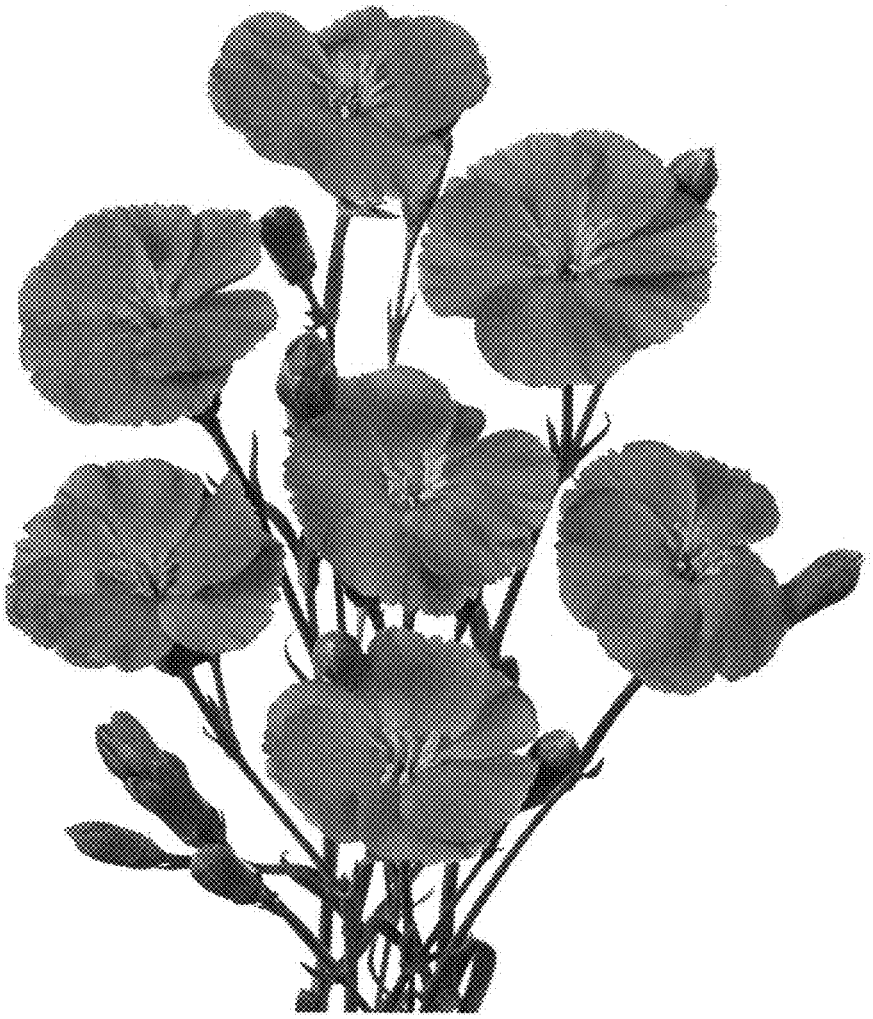

* * * * *